(12) United States Patent
Hoag et al.

(10) Patent No.: US 7,828,805 B2
(45) Date of Patent: Nov. 9, 2010

(54) HIP STEM CENTRALIZER DATUM GUIDE, AND METHOD

(75) Inventors: Stephen H. Hoag, Warsaw, IN (US); James L. Crumley, Fort Wayne, IN (US); Scott J Steffensmeier, Warsaw, IN (US); Erin M. Johnson, Columbia City, IN (US); Kevin S. Cook, Warsaw, IN (US); Archie W. Newsome, Mentone, IN (US); Bobby Chan, Warsaw, IN (US)

(73) Assignee: Zimmer Technology, Inc., Warsaw, IN (US)

( * ) Notice: Subject to any disclaimer, the term of this patent is extended or adjusted under 35 U.S.C. 154(b) by 779 days.

(21) Appl. No.: 11/346,069

(22) Filed: Feb. 2, 2006

(65) Prior Publication Data

US 2007/0179506 A1    Aug. 2, 2007

(51) Int. Cl.
*A61B 17/58* (2006.01)
*A61F 2/00* (2006.01)
*A61F 2/36* (2006.01)

(52) U.S. Cl. .................. 606/89; 606/86 R; 606/96; 623/22.12; 623/23.15; 623/23.48

(58) Field of Classification Search ..... 623/22.11–22.2, 623/22.4–23.38, 23.48; 606/92, 93, 95, 99, 606/102, 86 R, 87, 89, 96
See application file for complete search history.

(56) References Cited

U.S. PATENT DOCUMENTS

| 4,357,716 A | * | 11/1982 | Brown ........................ 606/94 |
| 4,698,063 A | | 10/1987 | Link et al. ............... 623/23.22 |
| 4,827,919 A | | 5/1989 | Barbarito et al. |
| 4,919,673 A | * | 4/1990 | Willert et al. ............ 623/23.48 |
| 4,927,422 A | * | 5/1990 | Engelhardt ................... 606/79 |
| 4,997,448 A | | 3/1991 | Filer |
| 5,041,117 A | * | 8/1991 | Engelhardt ................... 606/79 |
| 5,425,768 A | | 6/1995 | Carpenter et al. ........ 623/23.48 |

(Continued)

FOREIGN PATENT DOCUMENTS

CA    2059310    8/1992

(Continued)

OTHER PUBLICATIONS

International Search Report and Written Opinion mailed Jun. 19, 2007 in related International Application No. PCT/US2007/061437.

(Continued)

*Primary Examiner*—Todd E Manahan
*Assistant Examiner*—Ellen C Hammond
(74) *Attorney, Agent, or Firm*—Baker & Daniels LLP

(57) ABSTRACT

A hip stem centralizer datum guide and method are provided for positioning a proximal portion of a hip stem component within bone cement in an intramedullary canal of a femur. The datum guide is positionable in a predetermined position relative to the intramedullary canal and is able to create a datum that records the predetermined hip stem component position relative to the intramedullary canal. The datum is able to be referenced to position the hip stem component in the predetermined hip stem component position in the bone cement in the intramedullary canal.

16 Claims, 6 Drawing Sheets

U.S. PATENT DOCUMENTS

| | | | | |
|---|---|---|---|---|
| 5,480,453 | A * | 1/1996 | Burke | 623/23.21 |
| 5,571,202 | A | 11/1996 | Mathys et al. | 623/23.27 |
| 5,607,431 | A * | 3/1997 | Dudasik et al. | 606/80 |
| 5,658,351 | A | 8/1997 | Dudasik et al. | 623/23.48 |
| 5,702,485 | A | 12/1997 | Burke et al. | 623/23.21 |
| 5,725,596 | A * | 3/1998 | Burke | 623/23.21 |
| 5,746,771 | A * | 5/1998 | Clement et al. | 623/23.22 |
| 5,755,793 | A | 5/1998 | Smith et al. | |
| 5,792,143 | A | 8/1998 | Samuelson et al. | |
| 5,885,295 | A * | 3/1999 | McDaniel et al. | 606/86 R |
| 5,989,259 | A | 11/1999 | Penenberg et al. | 606/99 |
| 6,165,177 | A * | 12/2000 | Wilson et al. | 606/100 |
| 6,174,335 | B1 * | 1/2001 | Varieur et al. | 623/22.12 |
| 6,179,877 | B1 * | 1/2001 | Burke | 623/22.12 |
| 6,245,113 | B1 | 6/2001 | Revie et al. | 623/23.46 |
| 6,267,785 | B1 * | 7/2001 | Masini | 623/23.22 |
| 7,338,496 | B1 * | 3/2008 | Winslow et al. | 606/87 |
| 2002/0052661 | A1 | 5/2002 | Spotorno et al. | 623/23.48 |
| 2003/0149486 | A1 | 8/2003 | Huebner | |
| 2005/0090904 | A1 | 4/2005 | Howie et al. | |
| 2007/0179630 | A1 | 8/2007 | Benedict et al. | |
| 2008/0015708 | A1 | 1/2008 | Howie et al. | |

FOREIGN PATENT DOCUMENTS

| | | |
|---|---|---|
| EP | 1022001 A1 | 7/2000 |
| FR | 2770128 A1 | 4/1999 |
| GB | 2406055 A | 3/2005 |
| WO | WO96/24313 | 8/1996 |

OTHER PUBLICATIONS

Zimmer, Inc. CPT® Hip System, Primary Surgical Technique, 97-8333-202, © 1998.

U.S. Appl. No. 10/795,830, filed Mar. 8, 2004, Grimm.

U.S. Appl. No. 10/795,621, filed Mar. 8, 2004, Grimm.

U.S. Appl. No. 10/979,734, filed Nov. 2, 2004, Grimm.

U.S. Appl. No. 11/287,839, filed Nov. 28, 2005, Heavener.

Zimmer, Inc., VerSys® Hip System, Advocate™, V-Lign® and non V-Lign® Cemented Hip Prosthesis: Surgical Technique for Primary Hip Arthroplasty, 97-7850-02, © 2002.

Zimmer, Inc., CPT® Collarless Polished Taper Hip System, Brochure, 97-8333-03, © 1994.

Zimmer, Inc., VerSys® Hip System, Traditional Design, Innovative Featuers., Advocate™ Hip Prosthesis, Brochure , 97-7850-01, © 2002.

International Search Report and Written Opinion mailed Jun. 19, 2007 in related International Application No. PCT/US2007/061437.

* cited by examiner

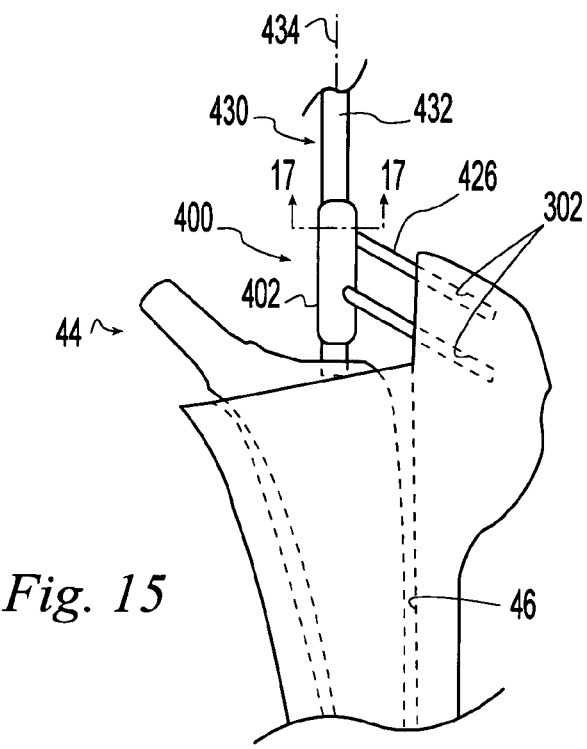
*Fig. 15*
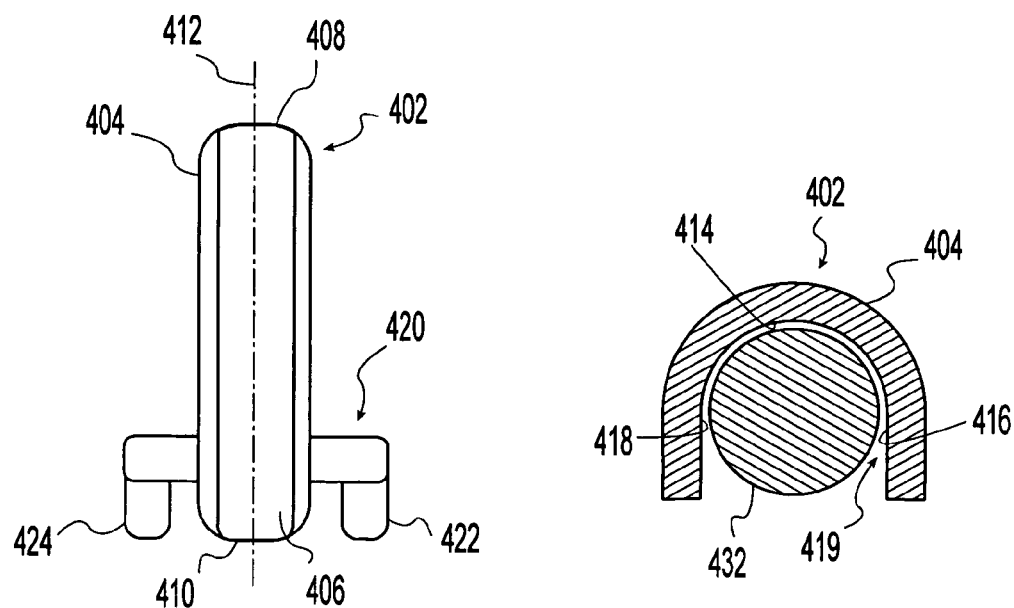
*Fig. 16*  *Fig. 17*

HIP STEM CENTRALIZER DATUM GUIDE, AND METHOD

FIELD OF THE INVENTION

The present invention relates to total hip arthroplasty. More particularly, the present invention relates to a proximal centralizer for a cemented hip stem and a method for its use.

BACKGROUND

Total hip arthroplasty is often used to restore function to a diseased or injured hip joint. Positions and directions relative to the hip joint may be described in terms of proximal being nearer the hip joint, distal being further from the hip joint, anterior being nearer the front of the body, posterior being nearer the back of the body, medial being nearer the centerline of the body, and lateral being further from the center line of the body. In total hip arthroplasty (FIGS. 1-2), the articular surfaces of the femur and pelvis are cut away and replaced with prosthetic implant components. In a typical case, the implants include a hip stem component 10, a femoral head component 12, an acetabular component 14, and bone cement 16. The hip stem component includes a stem portion 18 extending down into the intramedullary canal 20 of the femur 22 and a neck portion 24 extending away from the femur 22 to support the femoral head component 12.

The femur 22 is prepared by reaming the intramedullary canal 20 down into the bone along an axis 26 from a proximal position near the hip joint at the upper end of the femur 22 toward a distal position nearer the knee joint at the lower end of the femur 22. The pelvis 28 is prepared by reaming the acetabulum 30. Bone cement 16 is introduced into the prepared intramedullary canal 20 and acetabulum 30 and the prosthetic components are seated in the bone cement 16 so that it hardens around and locks the components in place. Positioning the hip stem component 10 in the correct orientation within the cement 16 is important for proper biomechanical functioning and long term stability. It is desirable to have a uniform and strong cement mantle 16 proximally around the anterior 34, lateral 36, and posterior 38 portions of the stem component 10. Proper placement further results in appropriate loading of the implants. Hip stem components, especially collarless ones, are sometimes placed at the wrong angle in the mediolateral direction. The typical situation is a varus placement in which the angle between the neck 24 and femoral axis 26 is too shallow. Hip stem centralizers have been proposed that are implanted in the cement mantle between the hip stem component and the intramedullary canal. These prior art centralizers necessitate the expense of an additional implantable component and reduce the contact area between the bone cement and the hip stem component.

SUMMARY

The present invention provides a hip stem centralizer datum guide and method for positioning a proximal portion of a hip stem component within bone cement in an intramedullary canal of a femur.

In one aspect of the invention, a combination includes a datum guide for being positioned in a predetermined position relative to the intramedullary canal and for creating a datum that records a predetermined hip stem component position relative to the intramedullary canal. The combination is further capable of referencing the datum to position the hip stem component in the predetermined hip stem component position in the bone cement in the intramedullary canal.

In another aspect of the invention, a combination includes a datum guide and a hip stem inserter. The datum guide includes a base positionable adjacent to the intramedullary canal in a predetermined position relative to the intramedullary canal and a cut guide mounted to the base. The cut guide is able to guide a cutter to cut a datum into the proximal portion of the femur that records a predetermined hip stem component position relative to the intramedullary canal. The hip stem inserter is engageable with the hip stem component in axial, medial/lateral, and anterior/posterior force transmitting relationship. The hip stem inserter includes a portion engageable with the datum. The hip stem inserter is simultaneously engageable with the hip stem component and the datum to position the hip stem component in the predetermined hip stem component position in the bone cement in the intramedullary canal.

In another aspect of the invention, a method includes positioning a datum relative to the intramedullary canal; creating a datum on the femur using the datum guide, the datum recording a desired hip stem component position in persistent manner such that the datum remains after the datum guide is removed; introducing bone cement into the intramedullary canal; inserting the hip stem component into the bone cement in the intramedullary canal; and referencing the datum to position the hip stem component in the desired position.

BRIEF DESCRIPTION OF THE DRAWINGS

Various examples of the present invention will be discussed with reference to the appended drawings. These drawings depict only illustrative examples of the invention and are not to be considered limiting of its scope.

FIG. 15 is an anterior elevation view of a datum sleeve according to the present invention useable in combination with the datum guides of FIGS. 5-13. The datum sleeve is shown in use to position a hip stem in an intramedullary canal.

FIG. 16 is a medial elevation view of the datum sleeve of FIG. 15.

FIG. 17 is a cross sectional view taken along line 17-17 of FIG. 15.

DESCRIPTION OF THE ILLUSTRATIVE EXAMPLES

Figure 1:
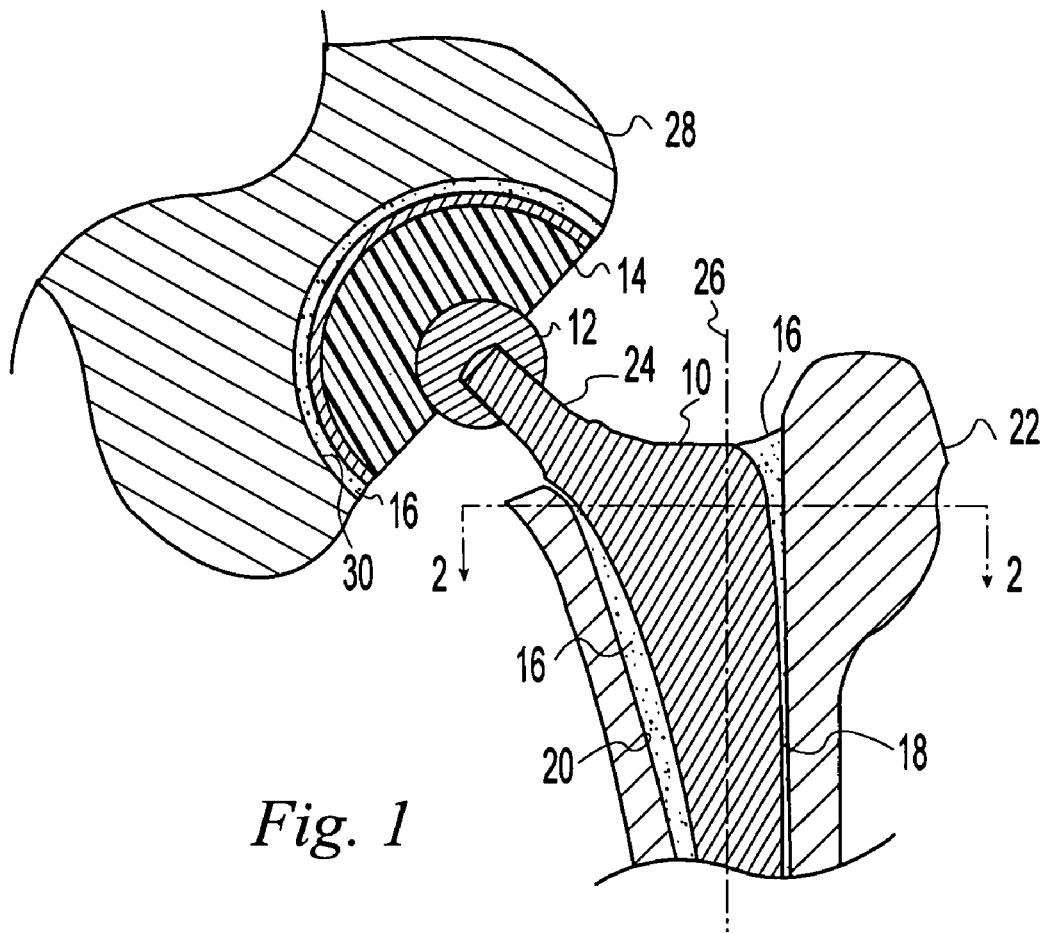
FIG. 1 is an anterior sectional view of a total hip prosthesis implanted in a hip joint.
Figure 2:
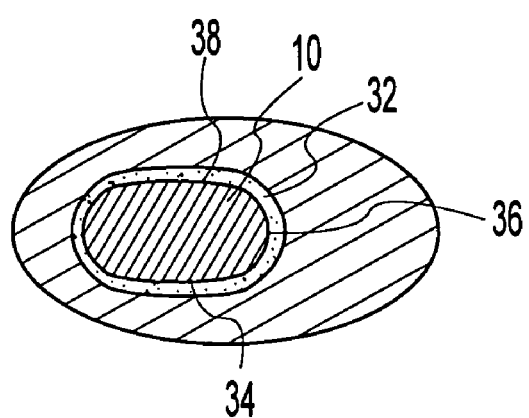
FIG. 2 is a sectional view taken along line 2-2 of FIG. 1.

Embodiments of a hip stem centralizer datum guide include a body positionable adjacent to the proximal portion of a femur and having a guide element for guiding the establishment of a datum on the proximal femur. The datum is subsequently able to be referenced to guide positioning of the proximal portion of a hip stem component within the intramedullary canal of the femur. For example, the datum guide may be used to establish a datum that records a desired medial/lateral position, anterior/posterior position, proximal/distal position, varus/valgus angle, anteversion/retroversion angle, and/or other hip stem component positioning parameter. The datum may be referenced upon insertion of a hip stem component to position the hip stem component in the desire recorded position. The datum may be referenced visually as a visual alignment aid. The datum may be positively engaged to physically constrain the insertion position. The datum may be referenced by the hip stem component, by an insertion instrument, and/or otherwise referenced. The datum guide facilitates creation of a persistent datum that remains after the datum guide is removed without requiring an additional implantable component and without interrupting or reducing the contact area between the hip stem component and bone cement within the intramedullary canal.

The body of the datum guide may be in the form of a rasp, reamer, provisional implant, guide rod, dedicated datum guide body, and/or other suitable body positionable adjacent to the proximal portion of the femur. The body may be positionable adjacent to the uncut proximal femur, on the cut surface of the proximal femur, in the intramedullary canal, and/or otherwise positionable adjacent to the proximal femur. For example, the body may engage portions of the prepared calcar region of the bone, the greater trochanter, the reamed intramedullary canal, and/or other portions of the proximal femur. The body may be positioned by engaging it with another item located adjacent to the proximal portion of the femur. For example, the body may be positioned by engaging it with a reamer, rasp, provisional implant, guide rod, and/or other suitable item. The body may be made of metal, plastic, ceramic, and/or other suitable materials.

The guide element may be in the form of reference marks, cutter guides, slots, holes, and/or other suitable guide elements. For example, a guide element in the form of reference marks may be used to align a datum on the proximal femur such as reference marks, slots, notches, holes, pins, and/or other suitable datum formed on or inserted into the proximal femur. For example, a guide element may take the form of reference marks on a rasp and/or provisional implant that are used to guide the formation of corresponding datum reference marks on the proximal femur. Similar reference marks may be provided on the hip stem component such that it may be positioned by aligning the reference marks on the hip stem component with the datum reference marks formed on the bone. The reference marks may be formed on the femur with a surgical pen, electrocautery, bur, chisel, and/or other suitable marking device.

The guide element may be in the form of a cutter guide for guiding a cutter to form a datum on the bone. For example, the cutter guide may be used to guide a saw blade, drill bit, mill, chisel, and/or other suitable cutter. The datum formed may be in the form of a slot, notch, hole, and/or other suitable datum. For example, the guide element may guide a cutter to form a slot and/or hole on the bone that is engaged by the hip stem component and/or insertion instrument to position the hip stem component in a desired position. The datum may be in the form of a pin, sleeve, rail, and/or other suitable datum engaged with a feature cut into the bone. For example, the guide element may guide a cutter to form a slot and/or hole on the bone and the datum may include a pin and/or sleeve inserted into the hole. The pin and/or sleeve may be engaged by the hip stem component and/or insertion instrument to position the implant in a desired position.

Figure 3:
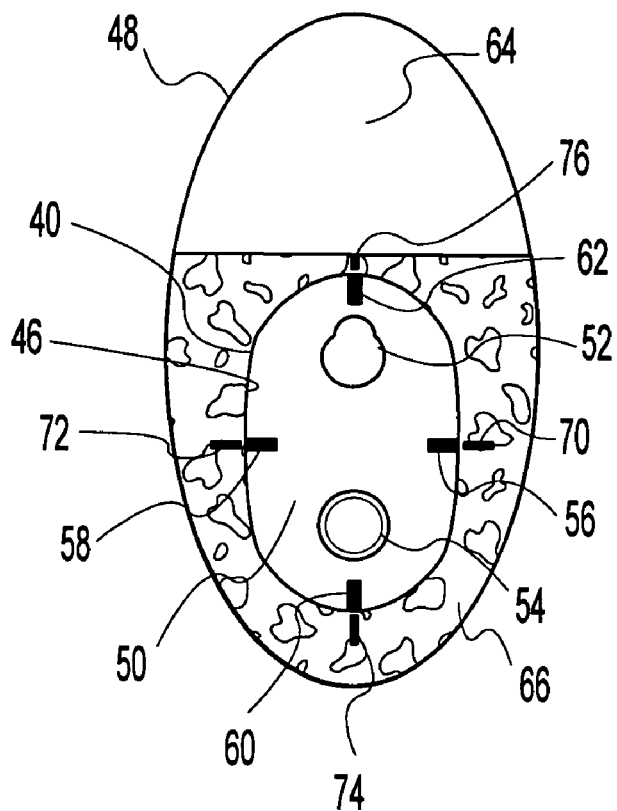
FIG. 3 is a distal plan view of a datum guide in use to establish a hip stem centralizer datum on a femur according to the present invention.
Figure 4:
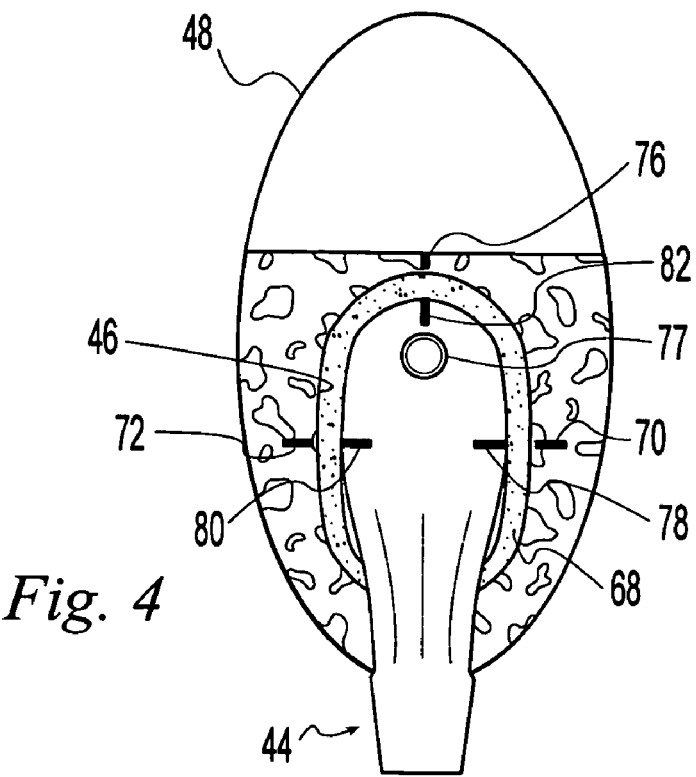
FIG. 4 is a distal plan view of a hip stem being positioned in an intramedullary canal using the datum of FIG. 3.

FIGS. 3-4 illustrate an exemplary hip stem centralizer datum guide in the form of an intramedullary rasp 40 and a method for positioning a proximal portion of a hip stem component 44 within an intramedullary canal 46 of a femur 48. The rasp 40 includes a proximal surface 50 defining an opening 52 and a post 54 engageable with a handle (not shown) for inserting the rasp 40 into and removing it from the intramedullary canal 46. The proximal surface 50 of the rasp 40 includes datum guide elements in the form of reference marks 56, 58, 60, 62 positioned adjacent to its anterior, posterior, medial, and lateral sides respectively. The femur 48 includes a greater trochanter 64 and a cut calcar surface 66. In the illustrative example, the calcar surface 66 has been cut to form a generally planar surface. The intramedullary canal 46 is progressively rasped to form a cavity shaped for receiving the hip stem component 44 and bone cement 68 (FIG. 4). When the final rasp 40 is seated, it defines the desired depth and orientation for the hip stem component 44 relative to the intramedullary canal 46. The reference marks 56, 58, 60, 62 are transferred to the calcar surface 66 by forming corresponding datum marks 70, 72, 74, 76 on the calcar surface 66 with a pen. Bone cement 68 is introduced into the intramedullary canal 46 and the hip stem component 44 is inserted into the bone cement 68. Insertion may be aided by engaging an inserter (not shown) with an inserter hole 77 defined by the proximal portion of the hip stem component 44. The hip stem component 44 includes alignment reference marks 78, 80, 82 that are aligned with the datum marks 70, 72, 76 to position the proximal portion of the hip stem component 44 within the bone cement 68 at a desired position relative to the intramedullary canal. Aligning the hip stem component 44 with the datum marks 70, 72, 76 ensures proper positioning relative to the final rasp 40 position and a desired cement mantel 68 distribution around the hip stem component 44. Aligning the anterior and posterior alignment reference marks 78, 80 with the anterior and posterior datum marks 70, 72 establishes the medial/lateral position of the hip stem component. Aligning the lateral alignment reference mark 82 with the lateral datum mark 76 establishes the anterior/posterior position of the hip stem component 44. The position of the alignment reference marks on the hip stem component 44 is related to the position of the reference marks on the rasp 40 to produce a predetermined desired bone cement mantel thickness. The predetermined position of the hip stem component 44 relative to the intramedullary canal 46 may be varied by varying the relative position of the reference marks 56, 58, 60, 62 on the rasp 40 and the alignment reference marks 78, 80, 82 on the hip stem component 44.

FIGS. 5-8 illustrate an exemplary hip stem centralizer datum guide 100 and method for positioning a proximal portion of a hip stem component 44 within an intramedullary canal 46 of a femur 48. The datum guide 100 includes a body 102 having a guide portion 104, and a base 106 alignable with the prepared intramedullary canal 46. In the illustrative datum guide 100, the base 106 includes a distal surface 108 that rests on the prepared calcar surface 66 and a spigot 110 projecting distally below the distal surface 108 to engage the opening of the prepared intramedullary canal 46 to position the datum guide 100 relative to the intramedullary canal 46. The illustrative spigot 110 is continuous. However, it may be discontinuous such as in the form of tabs, posts, and/or other suitable form for engaging the intramedullary canal 46. The illustrative base portion 106 engages the opening to the intramedullary canal 46 directly. However, it may engage the intramedullary canal 46 indirectly such as by mounting on another member. For example, the base 106 may mount to the rasp 40 of FIG. 3 to position the datum guide 100 relative to the intramedullary canal.

Figure 5:
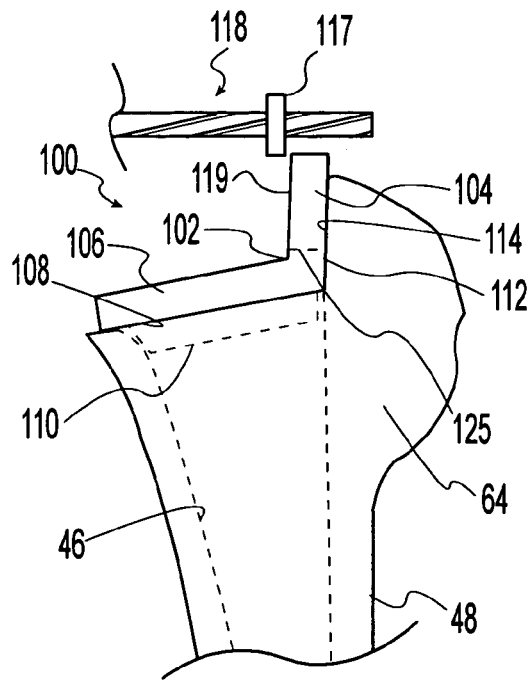
FIG. 5 is an anterior elevation view of a datum guide in use to establish a hip stem centralizer datum on a femur according to the present invention.
Figure 6:
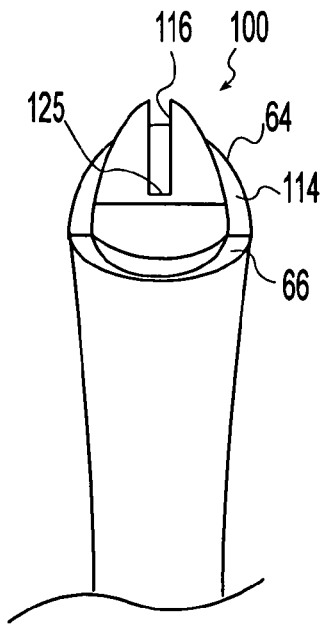
FIG. 6 is a medial elevation view of the datum guide of FIG. 5.

The illustrative base 106 is generally planar and the guide portion 104 extends upwardly at an angle from the base 106 to form a generally "L"-shaped body 102 (FIG. 5). The guide portion 104 includes a lateral surface 112 abuttable with a prepared medial surface 114 of the greater trochanter 64. The angle between the lateral surface 112 of the guide portion 104 and the distal surface 108 of the base 106 corresponds generally to the angle between the prepared surfaces 66, 114 of the calcar and greater trochanter 64. The guide portion 104 defines a cut guide slot 116 through the guide portion 104 to guide a cutter in the form of a side cutting mill 118.

Figure 7:
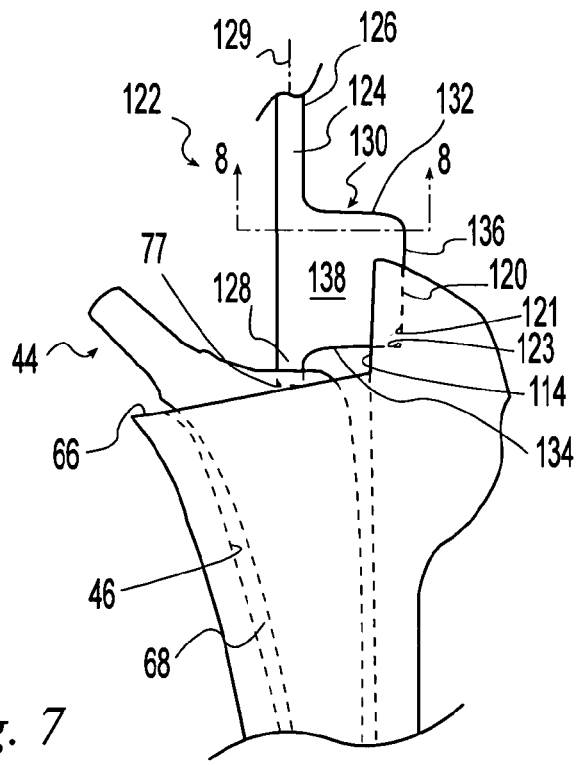
FIG. 7 is an anterior elevation view of a hip stem being positioned in an intramedullary canal using the datum of FIG. 5.
Figure 8:
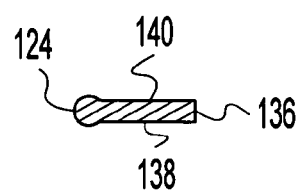
FIG. 8 is a cross sectional view taken along line 8-8 of FIG. 7.

In use, the femur is prepared by cutting the greater trochanter 64, cutting the calcar surface 66, and reaming and rasping the intramedullary canal 46 to receive the hip stem component 44. The datum guide 100 is positioned relative to the intramedullary canal 46, and the mill 118 is guided in cut guide slot 116 to cut a notch 120 into the proximal femur 48. The cut guide slot 116 has a width corresponding to the width of the mill 118. In the illustrative example, the datum guide 100 is used to form a medially facing datum notch 120 in the greater trochanter 64 having a width corresponding to the mill 118 width. The datum notch 120 has a depth defined by a lateral side wall 121 (FIG. 7). The depth of the datum notch 120 is controlled by a depth stop in the form of a collar 117 extending radially outwardly from the mill 118. The collar 117 abuts a medial surface 119 of the guide portion 104 to limit the penetration of the mill 118 into the greater trochanter 54. The datum notch 120 has a length defined by a distal side wall 123 (FIG. 7). The length of the datum notch 120 is controlled by the length of the cut guide slot 116. The mill 118 abuts a distal end 125 of the cut guide slot 116 to limit the length of the datum notch 120.

Figure 9:
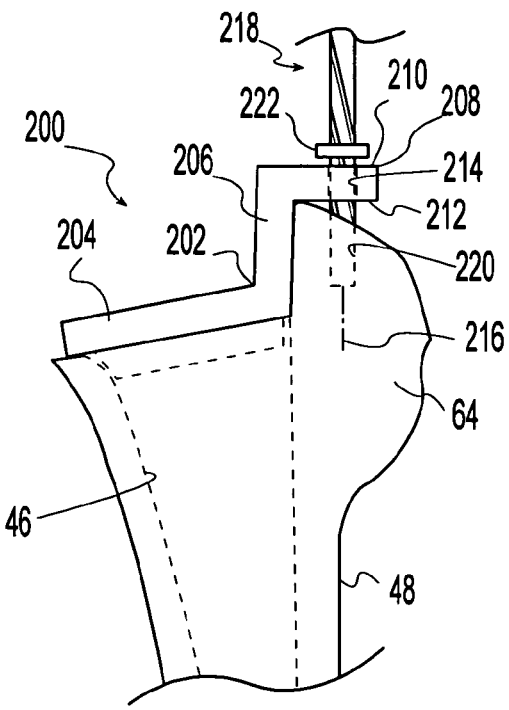
FIG. 9 is an anterior elevation view of a datum guide in use to establish a hip stem centralizer datum on a femur according to the present invention.
Figure 10:
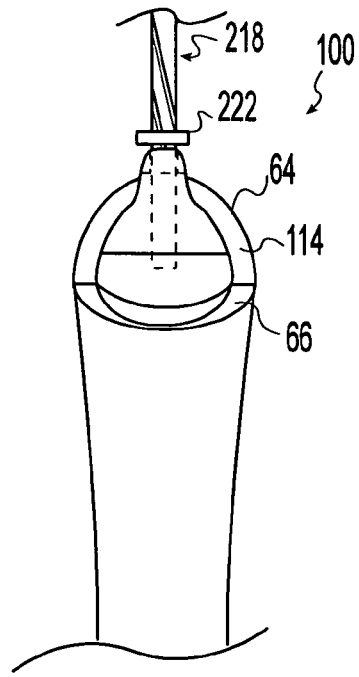
FIG. 10 is a medial elevation view of the datum guide of FIG. 8.
Figure 11:
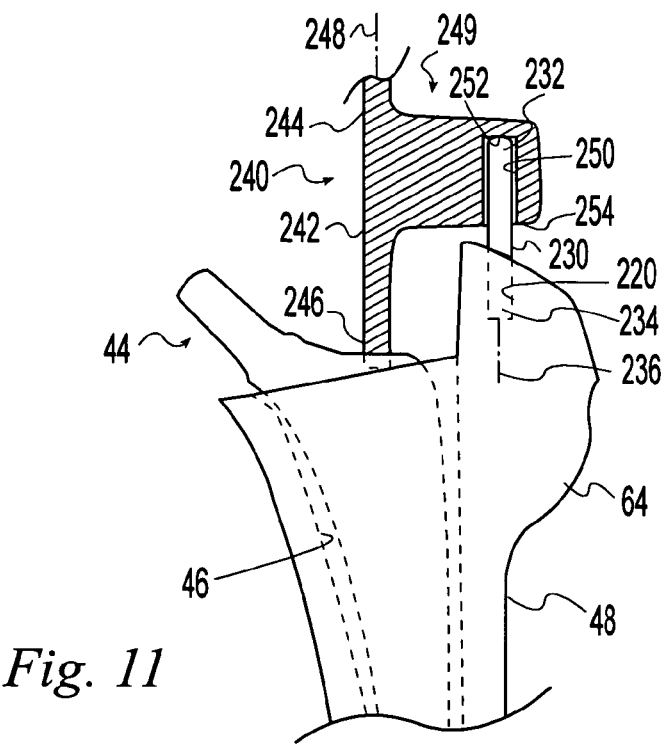
FIG. 11 is an anterior elevation view of a hip stem being positioned in an intramedullary canal using the datum of FIG. 8.

The mill 118 and datum guide 100 are removed from the femur 48. Bone cement 68 is introduced into the intramedullary canal 46 and an inserter 122 is engaged with the hip stem component 44. The inserter 122 includes a shaft 124 having a proximal end 126, a distal end 128, and a longitudinal axis 129 extending between the proximal and distal ends 126, 128. The distal end 128 engages the inserter hole 77 in the proximal end of the hip stem component 44 in axial, medial/lateral, and anterior/posterior force transmitting relationship such that when the inserter 122 is moved and tilted medial/laterally the hip stem component 44 moves and tilts medial/laterally and when the inserter 122 is moved and tilted anterior/posteriorly the hip stem component 44 moves and tilts anterior/posteriorly. The hip stem component 44 is inserted into the bone cement 68 in the intramedullary canal 46 and pressed distally with the inserter 122. As the hip stem component 44 nears its final seated position, a datum engaging tab 130 projecting laterally from the inserter shaft 124 engages the datum notch 120. The tab 130 includes a proximal surface 132, a distal surface 134, a lateral surface 136, and opposed anterior and posterior side walls 138, 140 defining the tab width. The side walls 138, 140 are spaced apart to define a close sliding fit of the tab 130 in the datum notch 120 to set the anterior/posterior position of the hip stem component. Abutting the distal surface 134 of the tab 130 with the distal side wall 123 of the datum notch sets the insertion depth of the hip stem component 44. Abutting the lateral surface 136 of the tab 130 with the lateral sidewall 121 of the datum notch 120 sets the medial/lateral position of the hip stem component 44. The predetermined position and depth of the datum notch 120 and consequently the position of the hip stem component 44 can be varied relative to the intramedullary canal 46 by varying the position of the guide slot 116, the length of the guide slot 116, and/or the collar 117 position, FIGS. 9-11 illustrate another exemplary hip stem centralizer datum guide 200 and method for positioning a proximal portion of a hip stem component 44 within an intramedullary canal 46 of a femur 48. The datum guide 200 and method of FIGS. 9-11 are similar to the datum guide 100 and method of FIGS. 5-8. However, rather than forming a datum notch 120 in the femur 48, a datum hole 220 is formed in the femur 48 for receiving a datum pin 230. The illustrative datum guide 200 includes a body 202, a base 204, and a guide portion 206 generally configured like the example of FIG. 5. However, the guide portion 206 includes a drill guide 208 extending laterally over the greater trochanter 64. The drill guide 208 includes a proximal surface 210, a distal surface 212, and a guide hole 214 through the drill guide 208 from the proximal surface 210 to the distal surface 212 along an axis 216. A drill bit 218 is guided by the guide hole 214 to form the datum hole 220 in the femur. In the illustrative example, the datum hole 220 is formed proximal-to-distal in the greater trochanter. The depth of the datum hole 220 is limited by a stop collar 222 projecting radially from the drill bit 218 to abut the proximal surface 210 of the drill guide 208. The datum pin 230 engages the datum hole 220 to position the datum pin 230 in a desired medial/lateral and anterior/posterior orientation relative to the intramedullary canal. The datum pin 230 may be permanently attached to the inserter 240 such that the datum pin 230 engages the datum hole upon insertion of the hip stem component 44. Alternatively, and as shown in FIG. 11, the datum pin 230 may be provided separate from the inserter 240 and pre-positioned in the datum hole 220 prior to insertion of the hip stem component.

The datum pin 230 includes proximal end 232, a distal end 234, and a longitudinal axis 236 extending between the proximal and distal ends 232, 234. The distal end 234 forms a close sliding fit with the datum hole 220 such that it is insertable axially into the datum hole 220 to orient the datum pin 230 coaxially with the datum hole 220. The distal end 234 of the datum pin 230 rests on the bottom of the datum hole 220 and the proximal end 232 of the datum pin 230 extends proximally a predetermined height relative to the intramedullary canal 46.

The inserter 240 includes a shaft 242 having a proximal end 244, a distal end 246, and a longitudinal axis 248 extending between the proximal and distal ends 244, 246. A datum engaging tab 249 projects radially outwardly from the shaft 242 and defines a socket 250 with a closed proximal end wall 252 and a distal opening 254. The socket 250 receives the datum pin 230 in close axial sliding relationship to orient the inserter 240 relative to the datum pin 230. The engagement of the socket 250 with the datum pin 230 spaces the inserter 240, and consequently the hip stem component 44, medial/laterally in a predetermined position relative to the intramedullary canal as established by the datum guide 200. The axis 236 of the datum pin 230 is generally parallel to the insertion axis 248 such that the datum pin 230 guides the hip stem component 44 along the insertion axis 248.

The illustrative datum pin 230 and socket 250 have round cross sections such that the inserter 240 can rotate about the datum pin 230 and permit the user to establish the anterior/posterior position of the hip stem component manually such as by visualizing the cement mantel thickness anteriorly and posteriorly. Alternatively, the datum pin 230 and socket 250 may be rotationally keyed such as with grooves, tabs, splines, non-circular cross sections, and/or other rotational keying mechanisms such that the datum pin 230 and socket 250 also establish the anterior/posterior position of the hip stem component 44. The datum pin 230 abuts the proximal end wall 252 of the socket 250 to set the depth of the hip stem component 44. The predetermined depth of the hip stem component 44 may be varied by varying the depth of the datum hole 220, the depth of the socket 250, and/or the length of the datum pin 230. Alternatively, the socket 250 may be formed through the tab 249 so that the datum pin does not bottom and the hip stem component 44 depth can be set using other depth setting features. The predetermined medial/lateral and anterior/posterior position of the hip stem component 44 may be varied by varying the position and orientation of the guide hole 214 relative to the intramedullary canal 46 and the position and orientation of the socket 250 in the tab 249. In the illustrative method, the datum hole 220 is predrilled and the datum pin 230 is subsequently inserted into the datum hole 220. Alternatively, the datum pin 220 may be guided directly by the guide portion 206 to simultaneously insert the datum pin 230 and form the datum hole 220.

Figure 12:
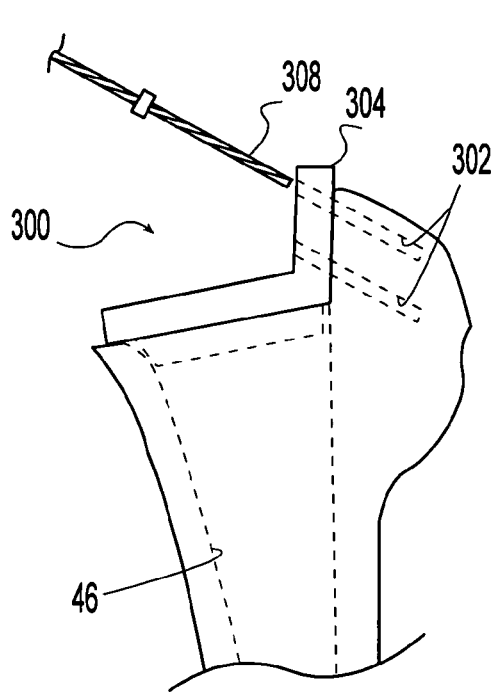
FIG. 12 is an anterior elevation view of a datum guide in use to establish a hip stem centralizer datum on a femur according to the present invention.
Figure 13:
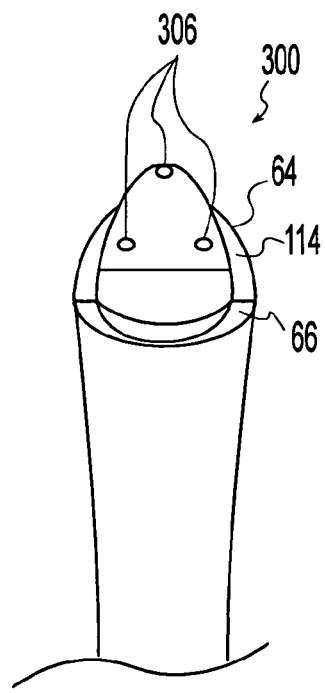
FIG. 13 is a medial elevation view of the datum guide of FIG. 11.
Figure 14:
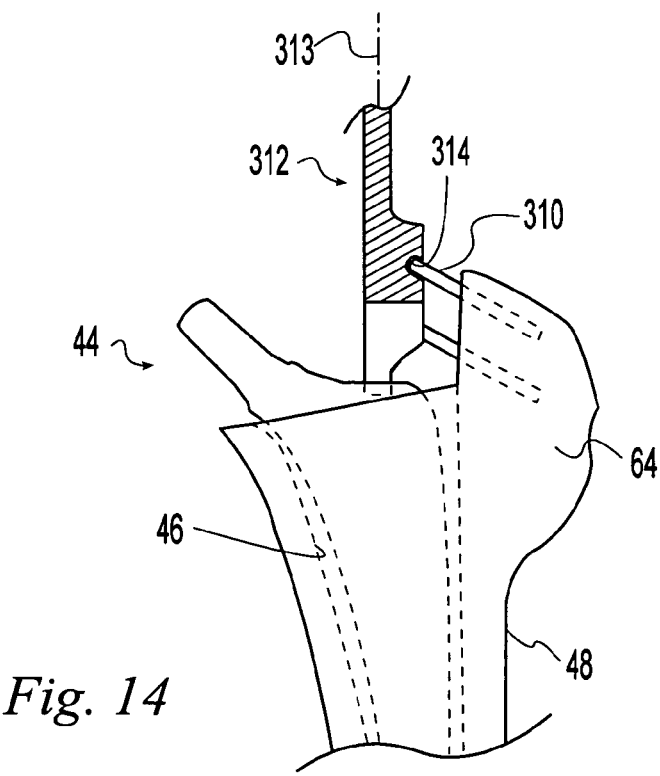
FIG. 14 is an anterior elevation view of a hip stem being positioned in an intramedullary canal using the datum of FIG. 11.

FIGS. 12-14 illustrate another exemplary hip stem centralizer datum guide 300 and method for positioning a proximal portion of a hip stem component 44 within an intramedullary canal 46 of a femur 48. The datum guide 300 and method of FIGS. 12-14 are similar to the datum guide 200 and method of FIGS. 9-11. However, rather than forming a datum hole 220 distally into the greater trochanter 64, a plurality of datum holes 302 are formed at an angle into the medial cut surface 114 of the greater trochanter 64. In the illustrative example, three datum holes 302 are formed in a triangular hole pattern. A drill guide portion 304 of the datum guide 300 includes guide holes 306 to guide a drill bit 308 to form the datum holes 302. Datum pins 310 are engaged with the datum holes 302 to establish a hip stem component 44 seating datum relative to the intramedullary canal 46. An inserter 312 includes an insertion axis 313 and further includes notches 314 for engaging the datum pins 310 to establish the medial/lateral position, anterior/posterior position, and depth of the hip stem component 44 relative to the intramedullary canal. The datum holes 302 are formed transverse to the insertion axis 313 such that the inserter 312 and hip stem component 44 move distally and laterally as the inserter engages the datum pins 310. In the illustrative method, the datum holes 302 are predrilled and the datum pins 314 are subsequently inserted into the datum holes 302. Alternatively, the datum pins 314 may be guided directly by the guide portion 304 to simultaneously insert the datum pins 314 and form the datum holes 302.

FIGS. 15-17 illustrate a datum in the form of a datum sleeve 400 configured for engagement with the datum holes 302 of FIGS. 12-14. The datum sleeve 400 includes a sleeve 402 having a convex outer surface 404, a concave inner bearing surface 406, a proximal end 408 and a distal end 410 oriented along a longitudinal axis 412. The inner surface 406 includes a lateral portion 414, an anterior portion 416, and a posterior portion 418. The sleeve 402 includes a medial opening 419 defined by an open medial side from the proximal end 408 to the distal end 410. An outrigger 420 extends from the sleeve 402 and includes an anterior leg 422, a posterior leg 424, and a lateral leg 426. All three legs extend laterally and distally from the sleeve parallel to one another for insertion into the datum holes 302. With the outrigger legs 422, 424, 426 inserted into the datum holes 302 the sleeve 402 is supported with its inner surface 406 at a desired orientation relative to the intramedullary canal 46 of the femur 48. An inserter 430 includes a longitudinal shaft 432 having a longitudinal axis 434. The inserter shaft 432 is received in the sleeve 402 in axial sliding arrangement. As the hip stem component 44 is inserted into the intramedullary canal 46, the inserter shaft 432 is moved laterally through the sleeve opening 419 to engage the shaft 432 with the lateral, anterior, and posterior portions 414, 416, 418 of the inner surface 406. The lateral portion 414 spaces the shaft 432 and consequently the hip stem component 44 a predetermined distance from the lateral side of the intramedullary canal 46. The anterior and posterior portions 416, 418 position the shaft 432 and hip stem component 44 anterior/posteriorly relative to the intramedullary canal 46. The shaft 432 may optionally include a depth stop (not shown) for abutting against the proximal end 408 of the sleeve to set the hip stem component 44 insertion depth. The illustrative sleeve 402 receives the shaft 432 in close sliding relationship anteriorly and posteriorly (FIG. 17) such that the shaft 432 position is closely constrained anterior/posteriorly. The shaft 432 can move in and out of the sleeve 402 through the medial opening 419. However, positioning the shaft 432 against the lateral portion 414 of the sleeve 402 sets the medial/lateral position. In alternative embodiments, the sleeve may form a complete ring (not shown) fully enclosing the shaft 432 such that the shaft 432 and sleeve 402 are inserted together. In this alternative embodiment, as the hip stem component 44 is inserted into the intramedullary canal 46, the legs 422, 424, 426 are inserted into the datum holes 302 to position the hip stem component 44 relative to the intramedullary canal 46. The illustrative datum sleeve 400 has been shown configured to engage the datum holes 302 created with the datum guide 300 of FIGS. 12-14. However, the datum sleeve 400 may configured to engage the datum hole 220 created with the datum guide 200 of FIGS. 9-11, the datum notch 120 created with the datum guide 100 of FIGS. 5-8, and/or configured to engage other suitable datums.

Although examples of a hip stem centralizer datum guide and its use have been described and illustrated in detail, it is to be understood that the same is intended by way of illustration and example only and is not to be taken by way of limitation. The invention has been illustrated in use to create datums on the calcar and greater trochanter of the femur to space a hip stem component from the lateral side of the intramedullary canal during hip replacement surgery. The hip stem centralizer datum guide has also been illustrated in use to space the hip stem component anterior/posteriorly in the intramedullary canal and further it has been illustrated to set the depth of insertion of the hip stem component. However, the hip stem centralizer datum guide may be configured to create datums at other locations and to set other parameters of hip stem positioning. Accordingly, variations in and modifications to the hip stem centralizer datum guide and its use will be apparent to those of ordinary skill in the art, and the following claims are intended to cover all such modifications and equivalents.

What is claimed is:

1. A method for guiding the positioning of the proximal portion of a hip stem component within bone cement in an intramedullary canal of a femur, the femur having a proximal portion nearer the hip joint, a distal portion nearer the knee joint, and a medial portion toward the midline of a body, the proximal portion of the femur including a generally planar cut surface that is located in a cut plane and that extends laterally from the medial portion of the femur, the intramedullary canal defining a longitudinal axis of the femur, the method comprising:

positioning a datum guide relative to the intramedullary canal;

creating a datum on the femur using the datum guide, the datum located proximally of the cut surface, the datum recording a desired hip stem component position in persistent manner such that the datum remains after the datum guide is removed;

introducing bone cement into the intramedullary canal;

inserting the hip stem component into the bone cement in the intramedullary canal;

referencing the datum with a guide component to position the hip stem component in the desired position; and coupling an inserter to the hip stem component and engaging the inserter with the guide component to guide the inserter in known relationship to the intramedullary canal.

2. The method of claim 1 wherein positioning a datum guide comprises mounting a datum guide adjacent to the proximal portion of the femur in known relationship to the intramedullary canal, wherein creating a datum comprises cutting a feature into the proximal femoral bone, and wherein referencing the datum comprises engaging the guide component with the feature cut into the bone to guide the inserter in known relationship to the intramedullary canal to position the hip stem component within the bone cement, the hip stem component referencing the datum indirectly through the guide component.

3. The method of claim 2 further comprising removing the guide component from the feature cut into the bone after inserting the hip stem component into the bone cement.

4. The method of claim 1 wherein positioning a datum guide comprises mounting a datum guide adjacent to the proximal portion of the femur in known relationship to the intramedullary canal, and wherein creating a datum comprises inserting at least one pin into the proximal portion of the femur.

5. The method of claim 4 further comprising removing the at least one pin from the proximal portion of the femur after inserting the hip stem component into the bone cement.

6. The method of claim 1 wherein creating a datum comprises forming at least one depression on a greater trochanter of the femur.

7. A method for guiding the positioning of the proximal portion of a hip stem component within bone cement in an intramedullary canal of a femur, the femur having a proximal portion nearer the hip joint including a greater trochanter and a distal portion nearer the knee joint, the intramedullary canal defining a longitudinal axis of the femur, the method comprising:

positioning a datum guide relative to the intramedullary canal;

forming at least one depression in the greater trochanter of the femur using the datum guide;

introducing bone cement into the intramedullary canal;

inserting a guide component into the at least one depression in the proximal portion of the femur to position the hip stem component in a desired position;

coupling an inserter to the hip stem component and engaging the inserter with the guide component to guide the inserter in known relationship to the intramedullary canal;

inserting the hip stem component into the bone cement in the intramedullary canal; and after inserting the hip stem component, removing the guide component from the at least one depression in the proximal portion of the femur.

8. The method of claim 7 wherein forming at least one depression comprises drilling a plurality of holes into the femur.

9. The method of claim 8 wherein inserting a guide component comprises inserting a plurality of pins into the plurality of holes in the femur.

10. The method of claim 7 wherein forming at least one depression comprises drilling transversely into the greater trochanter of the femur relative to the longitudinal axis of the femur.

11. The method of claim 7 wherein the proximal portion of the femur includes a generally planar cut surface that extends laterally from a medial portion of the femur and forming at least one depression comprises removing bone from the femur proximal to the cut surface.

12. A method for guiding the positioning of the proximal portion of a selected hip stem component within bone cement in an intramedullary canal of a femur, the femur having a proximal portion nearer the hip joint, a distal portion nearer the knee joint, the femur including an inner wall that defines the intramedullary canal, the intramedullary canal defining a longitudinal axis of the femur, the method comprising:

providing a hip stem component;

after providing the hip stem component, coupling an inserter to the hip stem component wherein the inserter includes at least one notch;

positioning a datum guide relative to the intramedullary canal;

creating a datum on the proximal portion of the femur that is discontinuous with the inner wall that defines the intramedullary canal using the datum guide, the datum recording a desired position of the selected hip stem component in persistent manner such that the datum remains after the datum guide is removed, wherein creating the datum comprises inserting at least one pin into the proximal portion of the femur;

engaging the datum with the inserter to indirectly reference the hip stem component to the datum, wherein engaging the datum with the inserter comprises inserting the at least one pin into the at least one notch of the inserter;

introducing bone cement into the intramedullary canal; and inserting the hip stem component into the bone cement in the intramedullary canal.

13. The method of claim 12 further comprising removing the inserter from the hip stem component and the datum after inserting the hip stem component.

14. The method of claim 12 wherein creating a datum comprises forming at least one depression in the proximal portion of the femur.

15. The method of claim 14 wherein the at least one depression extends transversely relative to the longitudinal axis of the femur.

16. The method of claim 12 wherein creating a datum comprises removing bone from a greater trochanter of the femur.

* * * * *